(12) United States Patent
Jeon et al.

(10) Patent No.: US 7,419,822 B2
(45) Date of Patent: Sep. 2, 2008

(54) MICROFLUIDIC DEVICE FOR ENABLING FLUIDIC ISOLATION AMONG INTERCONNECTED COMPARTMENTS WITHIN THE APPARATUS AND METHODS RELATING TO SAME

(76) Inventors: Noo Li Jeon, 14 Joyce Ct., Irvine, CA (US) 92612; Carl Cotman, 10021 Fox Springs Rd., Santa Ana, CA (US) 92075; Anne M. Taylor, 510 La Mirada Ave., San Marino, CA (US) 91108

( * ) Notice: Subject to any disclaimer, the term of this patent is extended or adjusted under 35 U.S.C. 154(b) by 0 days.

(21) Appl. No.: 10/605,537

(22) Filed: Oct. 6, 2003

(65) Prior Publication Data

US 2004/0106192 A1 Jun. 3, 2004

Related U.S. Application Data

(60) Provisional application No. 60/416,278, filed on Oct. 4, 2002.

(51) Int. Cl.
*C12M 1/34* (2006.01)
(52) U.S. Cl. .............. 435/288.5; 435/297.1; 435/297.5; 435/288.7; 435/305.2; 422/101; 422/102

(58) Field of Classification Search .................. 435/368, 435/288.5, 297.2, 297.1, 297.5, 305.1–305.4; 422/102, 68.1; 204/601, 604
See application file for complete search history.

(56) References Cited

U.S. PATENT DOCUMENTS

| | | | |
|---|---|---|---|
| 5,296,375 A * | 3/1994 | Kricka et al. | 435/2 |
| 5,635,396 A * | 6/1997 | Fedun | 435/283.1 |
| 5,744,366 A * | 4/1998 | Kricka et al. | 436/63 |
| 5,773,222 A * | 6/1998 | Scott | 435/7.1 |
| 5,830,659 A * | 11/1998 | Stewart | 435/6 |
| 5,866,345 A * | 2/1999 | Wilding et al. | 435/7.21 |
| 6,540,895 B1 * | 4/2003 | Spence et al. | 204/450 |
| 2002/0168757 A1 * | 11/2002 | Kirk et al. | 435/288.5 |
| 2003/0003570 A1 * | 1/2003 | Kanegasaki et al. | 435/288.5 |
| 2004/0005720 A1 * | 1/2004 | Cremer et al. | 436/518 |

* cited by examiner

*Primary Examiner*—William H. Beisner
(74) *Attorney, Agent, or Firm*—Dalina Law Group, P.C.

(57) ABSTRACT

Embodiments of the invention are directed to a device that combines microfabrication, microfluidic, and surface micropatterning techniques to create a multi-compartment neuronal culturing device that has application across a number of different neuroscience uses. Devices configured in accordance with the invention allow directed growth of neurites and isolation of neurites from their cell bodies. The device can use hydrostatic pressure to isolate insults to one compartment and, thus, expose localized areas of neurons to insults. Due to the high resistance of the microgrooves for fluid transport, insults are contained in the neuritic compartment without appreciable leakage into the somal compartment for a certain period of time (e.g., over 15 h).

14 Claims, 12 Drawing Sheets

MICROFLUIDIC DEVICE FOR ENABLING FLUIDIC ISOLATION AMONG INTERCONNECTED COMPARTMENTS WITHIN THE APPARATUS AND METHODS RELATING TO SAME

This application claims priority from U.S. Provisional Patent Application No. 60/416,278 filed on Oct. 4th, 2002, entitled "Microfluidic Multi-Compartment Device for Neuroscience Research" and incorporated herein by reference.

BACKGROUND OF INVENTION

1. Field of the Invention

Embodiments of the invention described herein relate to the field of nanotechnology and are more specifically directed to a microfluidic multi-compartment device for neuroscience research.

2. Background

A multi-compartment culturing device for neuritic isolation was first described by Campenot for primary cultures of sympathetic neurons. In this method, a tissue culture dish is coated with collagen and parallel lines, spaced 200 um apart, are scratched along the surface of the dish. A three-compartment Teflon piece is sealed to a Petri dish with silicone grease and neurons are plated in the small central chamber of the Teflon piece. Nuerites grow outwards into the two other compartments on either side, aligning parallel to the scratches. Variations of the Campenot chamber have been used in studies of various types of long projection neurons. However the Campenot chamber did not work well when used to culture cortical and hippocampal neurons.

Ivins, et al. developed a chamber designed for cortical and hippocampal neuron cultures using a relatively short barrier distance (150 um versus 300 um in the classic Campenot chamber). These chambers use a glass coverslip fixed to hemisected Teflon tubing using Sylgard 184 (Dow Corning, Corning N.Y.). A small amount of silicone vacuum grease is applied to the bottom of the converslip using a dissecting microscope and the whole apparatus is placed on the tissue culture dish. Neurites extend through the vacuum grease barrier between the polystyrene and the coverslip, if the vacuum grease barrier is sufficiently thin. A problem with these devices is that the process of making the chambers is laborious and their successfulness is directly related to the skill level of the individual using the device. Additionally, there is no alignment of neurons and the apparatus is not compatible with live cell imaging, thus, the effects of insults were observed only after the cells were fixed.

SUMMARY OF INVENTION

Cell culture methods are a commonly used research technique that allows the systematic manipulation of a growth condition of cells. In cell culture the culture media and substrate can be varied under controlled conditions. With well known culturing techniques the entire cell is exposed to the same conditions. However, for purposes of conducting experiments this is not always advantageous. Some cells can be asymmetrical and parts of the cell specialized. Neurons, for example, are polarized and have many processes that extend over relatively long distances (e.g., axons). Embodiments of the invention provide a device that enables the researcher engineer microenvironments at a cellular level. The ability to control fluidic and surface properties at the micron-scale, appropriate for cell biology, using microfabrication processes provides new opportunities for investigating fundamental biological processes. A researcher may, for instance, selectively isolate and treat specialized portions or domains of the cell. The researcher can direct the sites of neuronal attachment and the orientation and length of neurite outgrowth by micropatterning techniques such as microcontact printing. Secondly, by maintaining fluidically isolated domains within the culture area researchers can deliver a series of positive or negative stimuli to the soma, axons or dendrites. Neurons represent an excellent cell type to illustrate the concept of selective isolation and treatment and are therefore used herein for purpose of example. Those of ordinary skill in the art, however, will recognize that neurons are a test case and that the device described herein has applicability to other types of cells or biological type applications.

Embodiments of the invention are directed to a microfabricated neuronal device that combines microfabrication, microfluidic, and surface micropatterning techniques to create a multi-compartment neuronal culturing device that has application across a number of different neuroscience uses. Glass or plastic culture dish surfaces may be patterned with molecules (e.g., poly-lysine and laminin) to guide attachment and growth and a microfabricated device with embedded microchannels is fabricated and sealed against the patterned substrate. Neurons placed inside the microfluidic device can be cultured until the axons and dendrites have grown across a barrier with embedded channels at which point positive or negative stimuli may be selectively applied to distal portions of the neurites. Because the device allows for active control and fluidic isolation of neuronal or other microenvironments it enables researchers to explore new avenues of research for neurodegenerative diseases. Researcher can, for instance, use the device to mimic changes that are predicted to occur in local microenvironments in the aging and diseased brain. The device, for instance, is useful in conducting Alzheimer's disease (AD) research where the ability to expose insults locally to portions of a neuron is desired. For instance using the device a researcher can control the sites of somal attachment, deposit gradients of attachment factors on the substrate, and maintain fluid phase gradients of trophic factors or neurotoxic insults. Because the device allows investigation into how neuritis and somas respond to different microenvironments the device has broad applicability in other areas of the neurosciences and is useful in conducting research relating to Spinal Cord Injury (SCI) and/or other injuries or diseases affecting the nervous system.

The device has at least two compartments connected by a region having micron-sized grooves at the bottom of a barrier region, while maintaining fluidic integrity. Use of an optically transparent polymer allows for live cell imaging and microfluidics provides a mechanism to isolate domains within the culture area with the ability to deliver positive or negative stimuli to the soma, axons, or dendrites. When substrate patterning methods are applied, the device can be configured to direct the sites of neuronal attachment, orientation, and length of neurite outgrowth.

The device is fabricated in one or more embodiments using soft lithography techniques, such as poly(dimethyl siloxane), PDMS. Once made, the PDMS device is placed on a tissue culture dish (polystyrene) or glass substrate, forming two or more compartments. These compartments are separated by a physical barrier in which a number of micron-size grooves are embedded to enable neurties (or some other portion of a cellular organism) to grow across the compartments while maintaining fluidic isolation. Volumes less than 2 ul each can be used. However, devices having compartments with greater or lesser volumes are still considered to fall within the scope of the invention. Cells can be plated into a somal (cell body)

compartment and after a period of time (approx. 3-4 days), neuritis extend into the neuritic compartment via the grooves. The small grooves connecting the two chambers have enough hydrostatic pressure difference between the two compartments that viability is achievable for many hours. In one or more embodiment of the invention, viability of the neurons in the devices is approximately between 50-70% after 7 days in culture; this is slightly lower but comparable to control grown on tissue culture dishes (70%-80%). Thus, healthy neuron morphology is evident in both the devices and controls.

Devices embodying one or more aspects of the invention have the ability through the introduction of hydrostatic pressure to isolate insults to one compartment and thus expose localized areas of neurons to insults applied in soluble form. For instance, small grooves connecting the two chambers (e.g., somal and neuritic) have enough resistance that a hydrostatic pressure difference between the two compartments results in the ability to contain and isolate a biomolecular insult (i.e., beta-Amyloid, MW=3-4 kD) in the lesser volume compartment for many hours (e.g., 15 or more). Thus insults can be contained in one compartment (e.g., the neuritic compartment) without appreciable leakage into the somal compartment.

Visualization and identification of neurons is feasible using poly-lysine patterning in combination with the microfluidic device. In one or more instances, the device is constructed to have multiple chambers. At least one of these chambers is configured to direct the sites of neuronal attachment and the orientation of neurite outgrowth by micropatterning techniques, combined with fluidically isolated compartments with the culture area. The ability to direct the sites of neuronal attachment and the orientation of neurite outgrowth by micropatterning techniques, combined with fluidically isolated compartments within the culture area offer significant advantages over standard open culture methods and other conventional methods for manipulating distinct neuronal microenvironments. The device may have two or more compartments thereby allowing the application of substances to more than one neurite location and can be applied to neuronal and non-neuronal cells.

DETAILED DESCRIPTION

Embodiments of the invention are directed to a Microfluidic Multi-Compartment Device for Neuroscience or other Research. In the following exemplary description numerous specific details are set forth in order to provide a more thorough understanding of embodiments of the invention. It will be apparent, however, to an artisan of ordinary skill that the present invention may be practiced without incorporating all aspects of the specific details described herein. The quantities and measurements contained herein are approximations that can in some instances be varied to any degree that enables the invention to accomplish the function for which it is designed. In other instances, specific features, quantities, or measurements well-known to those of ordinary skill in the art have not been described in detail so as not to obscure the invention. Readers should note, that although examples of the invention are set forth herein, the claims, and the full scope of any equivalents, are what define the metes and bounds of the invention.

Fabrication of Neuronal Devices The neuron culture device configured in accordance with one or more embodiments of the invention are created using microfabrication techniques, such as photolithography, to create a master mold with micron-resolution. Soft lithography is a cost effective method used to replicate chambers and devices from a "master" mold, usually using the elastomer, poly (dimethylsiloxane) (PDMS). Thus the devices may be fabricated for single use to minimize contamination and reproducibility issues. Because once a mold is formed replication of a PDMS device is relatively straight forward, the approach enables reproducible fabrication of a number of devices for each experimental run.

Figure 1:
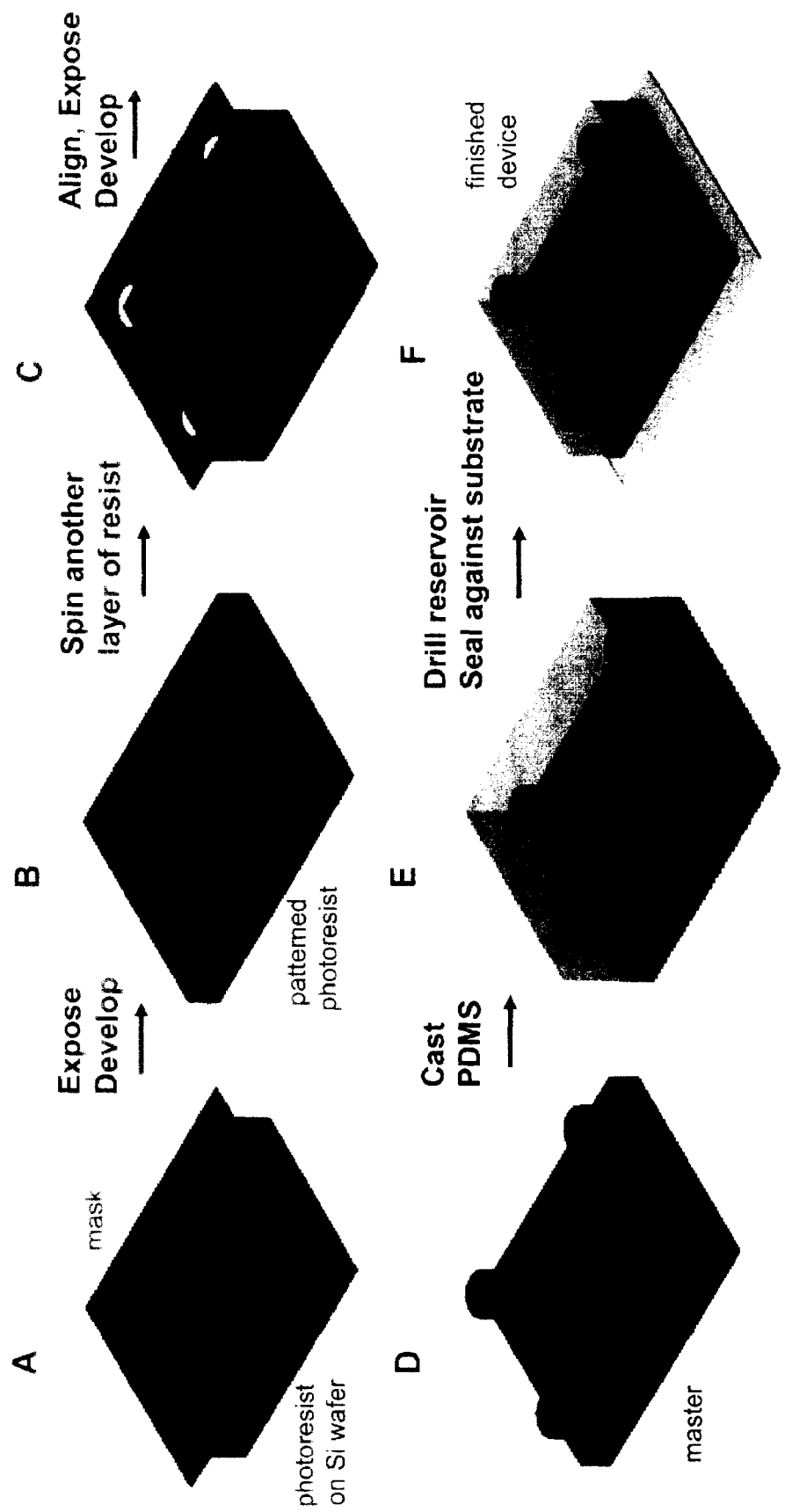
FIG. 1 illustrates a process for fabricating the neuron chamber configured in accordance with an embodiment of the invention.

FIG. 1 illustrates a process for fabricating a neuron chamber configured in accordance with an embodiment of the invention. The fabrication processes illustrated herein are given for purposes of example only and other methods for making the microfluidic device described are also contemplated as being part of the invention. As FIG. 1 shows, a top piece of the chamber is fabricated in PDMS by molding against a master that has a two-level photoresist pattern. Steps A and B show the formation of microgrooves (~3 um high and ~10 um wide) in the master using a thin photoresist layer. The size of the grooves is designed to limit the neurons in the somal chamber while allowing the growing neuritic processes to cross from one chamber to another. However, the sizes may vary depending on the circumstances and other sizes that also accomplish this same or a similar function are also considered part of the invention. Well-defined grooves with controlled dimension allow each chamber to function in a fluidically isolated manner. Steps C and D show the fabrication step for main compartments for somal and neurite chambers. Two chambers, separated by a barrier, form fluidically isolated areas that, for example, each hold less than 2 uL of fluid (100 um high, 1500 um wide, and 8 mm long). Other chamber arrangements involving more than 2 chambers and/or different shaped geometries are also contemplated as being within the scope of the invention. In the embodiment of the invention illustrated in FIG. 1, the top part of the device is formed by replica molding PDMS against the master (step E). Releasing the PDMS and sealing it to a flat substrate completes the neuron chamber fabrication (step F). In at least one instance the entire device can fit on a 1"×2" glass coverskip or a comparable substrate and compatible with phase or DIC and fluorescent microscopy. The device can be covalently bonded to glass via air plasma treatment or simply pressed down on polystyrene tissue culture dishes to create water tight-seals with the substrates.

As was mentioned above, the master for each device can be fabricated by patterning two layers of photoresist. More specifically, a high resolution printer (e.g., 20,000 dpi) may provide a mechanism for generating a first transparency mask from a CAD file in order to create a set of microchannels (e.g., approx. 10 um wide, spaced 50 um, although other variations are also contemplated). SU-8 5 photoresist can be spun on an air-plasma-cleaned silicon wafer at a rate of approximately 4000 rpm for approximately 60 s to obtain an approximate thickness of 3 um. The transparency mask can be used to pattern the SU-8 5 photoresist and SU-8 50 can be used as a second layer and spun at approximately 1000 rpm for approximately 60 s. A second mask may be used to create chamber areas (e.g., somal and neuritic chambers) by printing and aligning the second mask to the first pattern. In one embodiment of the invention the second mask is printed at approximately 5080 dpi with a resolution of approximately 35 um aligned to the first pattern. Although one of ordinary skill in the art will recognize that other masking alternatives are also available.

After developing, the wafer may be placed in a clean Petri dish and treated (e.g., with (tridecafluoro-1,1,2,2-tetrahydrocty) trichlorosilane) to facilitate removal of the PDMS from the master mold. PDMS can made using a 10:1 ratio of prepolymer and catalyst or using any other acceptable molding technique. The Petri dish containing the wafer can then be heated (e.g., in a dry oven for 1 hour at 70° C. and Ethanol or some other chemical with sterilizing properties can be used to sterilize the devices. Glass coverslips (22 mm_30 mm, no. 1 thickness, Proper) can be cleaned by sonication in an ethanol solution for 30 min and then treated in an air plasma cleaner for 10 min to remove residual materials from the surfaces. The tissue culture dishes and glass coverslips can coated with poly-L-lysine (Sigma) at 50 ug/ml in sterile H2O for 2 hours room temperature. The devices and tissue culture dishes are typically air-dried for a period of time (e.g., overnight) before use.

Culture of Embryonic Rat Cortical Neurons.

The device is adaptable for use in a variety of culture environments and may, for instance, be used to culture E18 rat cortical neurons or other neurons. For purposes of illustration the process of using cortexes of E18 rat embryos is described herein. However, as one of skill in the art will recognize after reading the invention described herein, the invention is not limited to this specific example, but has uses in many different culturing environments.

Briefly, cortexes of E18 rat embryos may be dissected in CMF-HBSS [calcium- and magnesium-free Hanks' balanced salt solution (HBSS) containing 1 mM pyruvate, 4.2 mM sodium bicarbonate, and 0.3% bovine serum albumin (BSA)], rinsed with CMF, and resuspended in a trypsin solution (0.125% trypsin in CMF-HBSS containing 0.5 mM EDTA) for 7 min at 37° C. or 25 min at ambient temperature. Trypsinization may be topped with Dulbecco's modified Eagle's medium (DMEM) containing 10% fetal calf serum, the tissue can then be centrifuged at 1000 rpm for 1 min, and the resulting cell pellet can be resuspended in 2 mL of culture medium (Neurobasal medium, Gibco 21103, containing B27 supplement, Gibco 17504, GlutaMAX, Gibco 35050, and penicillin-streptomycin, Gibco 15070). Following trituration through fire-polished Pasteur pipets with the diameter maximally 50% constricted, the cell suspension may be filtered through a 40 um cell strainer, and viability determined with trypan blue. Cells may be plated with densities from 1 to 4×106 cells/ml. For plating inside microfabricated devices, cell suspension can be diluted 25-fold from control to obtain comparable cell density per area.

Microscopy.

Phase contrast and epifluorescent images of cultures within the device can be taken using a digital image capture system (e.g., an inverted microscope NikonTE300, a CCD camera, and MetaMorph (Universal Imaging, Pa.). DG-4 can be used as an excitation light source which has an internal shutter controlled by MetaMorph in order to take time-lapse images at different excitation wavelengths. It is also feasible to use a motorized stage to take images at multiple locations throughout the samples. The benefit of using this or any other image technique is that it enables the researcher to monitor activity within the microfluidic device for purposes of observation. Thus, the invention contemplates the use of any image system adapted for use with the microfluidic device described herein.

Substrate PatterningIt is feasible to selectively absorb and pattern poly-Llysine on the surface of tissue culture dishes. The PDMS elastomeric mold, having (for example) 25 um lines and spaces with a depth of 50 um, can be cast from patterned silicon wafers generated with SU-8 50 by using photolithography. The degassed 10:1 mixture of elastomer and curing agent can then be poured over a master pattern and cured at 70° C. for 1 h. The PDMS mold can be sterilized with ethanol and allowed to dry for at least 1 h; a sterile tissue culture dish can be used as the substrate for the mold. A drop of a 50 ug/mL solution of poly-L-lysine (PLL) in sterile deionized (DI) water can be placed at an open end of the network of channels, which fills the channels by capillary action. After filling the channels, the solution is incubated for a period of time (e.g., one hour) to allow absorption onto the surface. After this step the PDMS mold is removed and a fresh buffer solution or sterile deionized water is used to wash away the excess solution.

Microcontact printing can be used to create poly-L-lysine on coverglass. The PDMS elastomeric stamp having 25 um lines and spaces with a depth of 10 um can be cast from patterned silicon wafers generated with SU-8 10 by using photolithography. The degassed 10:1 mixture of elastomer and curing agent can be poured over a master pattern and cured at 70° C. for 1 h. The elastomer stamp can be peeled away from the master pattern after cooling. The ink can be prepared under ambient atmosphere using a 5 mg/mL solution of octadecyltrichlorosilane (OTS) in a hexane solvent. The patterned face of the PDMS stamp can be coated with a solution of OTS by a spin-coating technique at 1500 rpm for 30 s, dried in a stream of argon for 30 s, and then placed on top of a precleaned glass surface and kept in contact with the inked stamp for 30 s. After contact printing, the OTS patterned sample can be rinsed thoroughly in isopropyl alcohol and immersed in a 50 ug/mL solution of PLL in water for 2 h. Once created, the sample can be rinsed in water and dried. Micropatterns on the glass substrates may be verified using fluorescence microscopy; the micropatterned surface can be exposed to a solution of 10 ug/mL fluorescein isothiocyanate (FITC; Molecular Probes, Eugene, Oreg.) in PBS (pH 7.4, 50 mM) at 37° C. for 30 min: the terminal-NH2 group reacts with the isothiocyanate group of FITC yielding FITC-conjugated PLL patterns. The patterned glass substrate can then be washed with DI water and ethanol.

Design of Neuronal Devices.

In one or more embodiments of the invention the neuronal culture devices are fabricated in PDMS. Making the devices using PDMS is beneficial (but not required) because: (1) PDMS is optically transparent and well suited for live cell imaging, (2) many molds can be made from the same master with reproducible results, (3) PDMS can be covalently sealed to glass using plasma bonding, and (4) a watertight seal can also be made with polystyrene or other flat substrates by conformal contact. Both glass and polystyrene tissue culture dishes can be used as substrates for the device.

It is possible to stay within the scope and spirit of the invention by adapting the shape and generalized arrangement of the neuronal culture devices described herein. Any device comprising at least two independent compartments (e.g., neuritic and somal compartments) and having a middle region, regardless of shape falls within the scope of the invention. In one or more embodiments of the invention the neuritic and somal compartments are connected by a middle region having a number of micro-grooves of a certain width, height, and length. Various sizes, shapes, configurations, and number of grooves are possible. For instance one multi-compartment device isolates somas to a single compartment, while allowing neuritis to grow through a barrier with embedded micron-sized channels into a chamber containing only neurites. The distance of the middle region can vary. For instance, when using cortical and hippocampal neuron cultures it may be necessary to optimize outgrowth by creating a chamber that allows neurites to enter the outer compartment after modest period of outgrowth. Chambers with a relatively short barrier distance (e.g., ~100 um versus ~300 um) are sometimes useful. Microfabrication techniques ensure the device is capable of fluidically isolating the somal and neuritic chambers while still allowing for neurites to grow through the barrier. The microfluidic device configured in accordance with one or more embodiments of the invention may have virtual or physical barrier regions.

In one embodiment of the invention, for instance, the device contains 120 grooves, 10 um wide, 3 um high, and 150 um in length. The grooves can be spaced, for instance, 50 um apart to prevent the grooves from collapsing. Other sizes of grooves and spacing are possible, but generally speaking the size of the grooves should be small enough that dissociated neurons during loading do not pass over to the adjoining neuritic compartment. This design simplifies the loading process and allows selective placement of neurons in one compartment.

In one embodiment of the invention holes are placed in each device that serve as loading inlets and cell medium reservoirs for nutrient and gas exchange. The device may, for instance, contain four holes (8 mm in diameter), two at either end of each compartment. When small holes (2.3 mm diameter) are used, the devices quickly dried out after a few days. Even if cell culture medium is added frequently, there is a low cell viability with such small holes due to poor exchange of nutrients, wastes, and gases such as $CO_2$. In an example embodiment, the volume in each covered compartment (i.e., without the reservoirs) is less than 2 uL. In comparison, the combined reservoirs for each compartment can hold up to 400 uL. By having such small culture volumes, reagent amounts can be reduced from traditional culturing methods.

After a varying time period (e.g., approximately 3-4 days) of growth, neurites from the somal compartment extend into the neuritic compartment. Although other rates of growth are feasible, the rate of neurite outgrowth in tests conducted using embodiments of the invention was between 50 and 100 um per day. After an appropriate amount of time (e.g., 7 days, or when an insult is desired) a quantity of medium (e.g., 15 uL) can be transferred from the neuritic compartment to the somal compartment, leaving a net volume difference (e.g., of 30 uL . . . assuming the volumes in the two compartments have equilibrated during the past 7 days). A solution (e.g., 5 uL) containing the insult can then be administered to the neuritic side. When performing these operations, it is important to use caution when adding and withdrawing equivalent amounts to wells on the same side in order to minimize convective flow effects.

Virtual Barrier.

Figure 11:
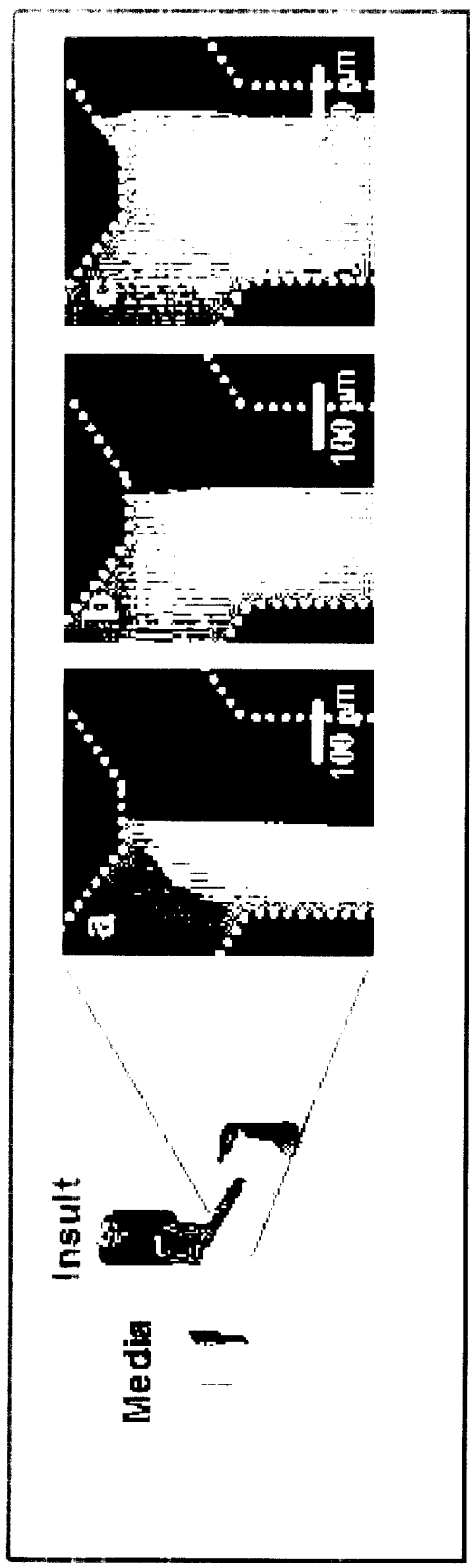
FIG. 11 illustrates a schematic representation of virtual barrier device and examples of virtual barriers between two fluorescently labeled solutions.

The virtual barrier chamber rely on the fact that the flow of liquids in capillaries often has a low Reynolds number (Re) and is laminar. When two or more streams with low Re are joined into a single stream, the combined streams flow parallel to each other without turbulent mixing. This ability to generate and sustain parallel streams of different solutions in capillaries between two streams can be utilized as a virtual barrier. By streaming different solutions containing media (green) and insult (red) over the neurons, the device can maintain a virtual barrier and expose only a select portion of the neuron to the stimuli or insult. FIG. 11 illustrates a schematic representation of virtual barrier device and examples of virtual barriers between two fluorescently labeled solutions. A PDMS piece containing Y-shaped microchannel embedded on its surface can be placed and bonded to a glass coverslip to form a network of channels. Fluids can be infused into the channel using syringe pumps as indicated in the scheme. The fluorescent micrograph show the junction where the two streams converge, one containing FITC labeled dextran (representative of media) and the other containing Texas Red labeled dextran (representative of insult). The relative width of the streams can be controlled by adjusting the relative volumetric flow rates of the streams. The volumetric ratio of Green/Red flow varied from 1, 3, and 5 for (A), (B), (C) respectively. FIG. 11 shows successful demonstration of the virtual barrier chamber. The microfluidic device can be prepared by placing a PDMS piece with embedded channels (300 um wide and 100 um high) onto a flat substrate. An embodiment of the invention can be fabricated as a "Y-shape" microchannel having two inlets that converge into a single main channel. The two inlets were attached to syringe pumps containing FITC-dextran (green) and Texas Red-dextran (red), respectively. By allowing different solutions to flow from the inlets, parallel streams of different liquids created in the main channel. Under these conditions, there is no turbulence and streams flow next to each other with diffusive mixing. The width of the stream and the position of the interface between adjacent streams can be controlled by adjusting the relative amounts of fluid injected into each inlet. As the ratio of flow rate for green/red solution was increased, the relative width of the green solutions increased in corresponding manner as shown in the series of fluorescent micrographs in FIG. 11a to 11c.

Figure 12:
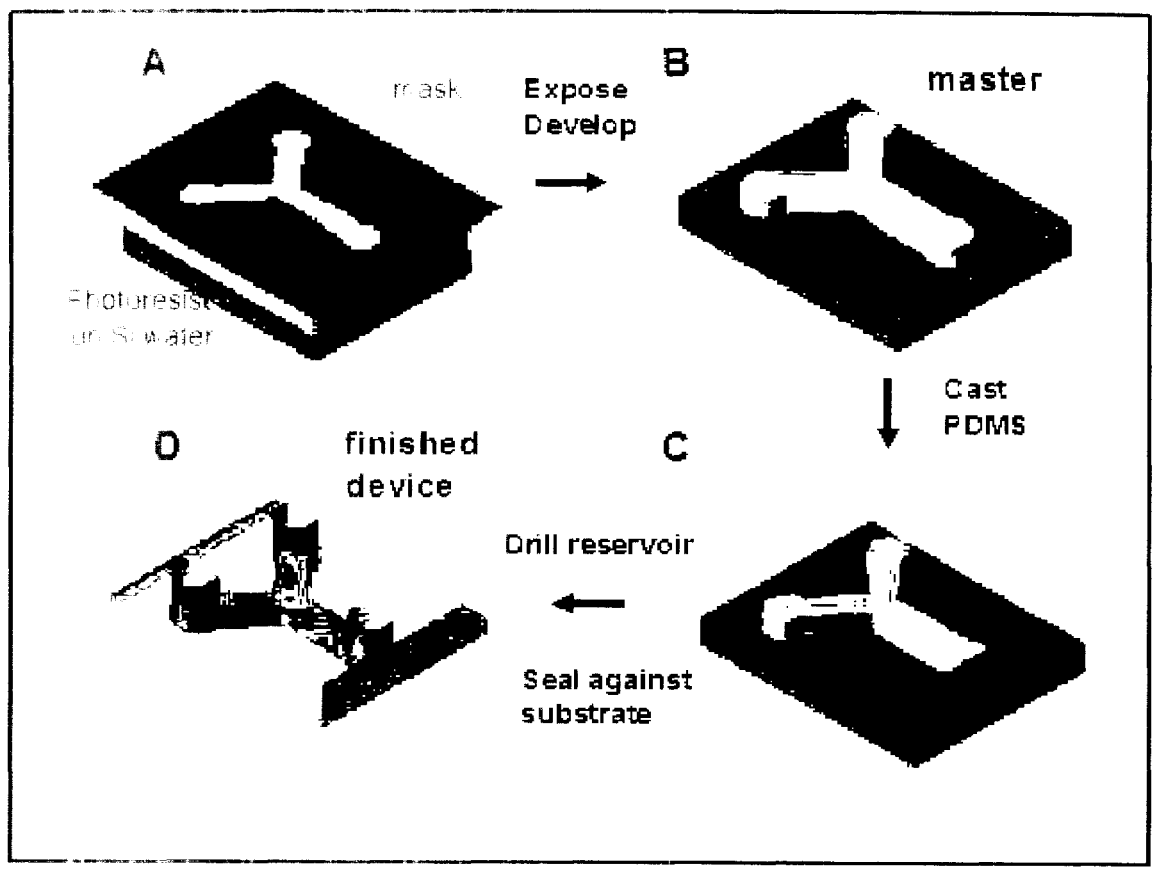
FIG. 12 illustrates a schematic for the fabrication of virtual barrier microfluidic neurochamber.

FIG. 12 illustrates a schematic for the fabrication of virtual barrier microfluidic neurochamber. This design uses a "Y-channel" design takes advantage of the laminar flow characteristics of flow behavior to selectively expose portions of neuron to apoptotic insults. However, designs having other geometries are feasible. Rapid prototyping of such custom devices can be performed in less than 24 hours. Therefore it is possible to try many different geometries. The process starts with designing the device layout using a CAD program from which a high-resolution transparency photomask will be generated. This photomask can be used to selectively expose a thick photoresist (light sensitive polymer) that was spun on a flat substrate (i.e. Si wafer), FIG. 12A. Developing the photoresist will leave a positive relief that can serve as a master mold having a positive relief (150 ?m) of "Y-shaped" microchannel, FIG. 12B. A negative relief of PDMS will be formed by casting and curing the prepolymer of PDMS against the positive master, FIG. 12C. This PDMS replica with embedded channel can be bonded against a glass substrate to produce the required systems of microfluidic channels and chambers. Inlet and outlet ports for the fluid and cells can be punched out of the PDMS using a sharpened tool, FIG. 12D. The completed device should be sterilized using ethanol and dried before use.

Physical Barrier The fabrication of physical barrier chamber is similar to the virtual barrier chamber except for an additional photolithography step to generate a series of small channels in the barrier which will allow neurons' processes to grow across the barrier while minimizing mixing of fluids. The first photolithography step (FIGS. 1A and 1B) generate relief of narrow and thin channels with dimensions less than 10 um. The length of the channels, which define the length of the barrier between the soma and neurite chambers, can vary from ~50 to ~200 um. Optimum width of barrier that allows neurites to grow across in reasonable time (several days) and yet perform reproducible barrier function depends on the situations of the test. The size as well as the density of these channels can be varied for optimal growth. The second photolithography step, FIGS. 1C and 1D, will define the microcompartments in which the neurons will be cultured. These areas will be relatively larger (150 um high, 1500 um wide, and 1.5 cm long) compared to the first pattern for the channels. Once the master mold is fabricated, PDMS prepolymer can be cast and cured to replicate the relief pattern and placed on a flat substrate to complete the device. Before assembling the PDMS with a substrate, holes for reservoir can be punched out in PDMS using a simple sharpened tool to allow addition and removal of media and other insults. Because the total volume of liquid to fill the chamber of this size is minute (~25 ul) compared to volumes needed for conventional Campenot chamber or Petri dish (several ml), the amount of insults and media required for the experiments is drastically reduced.

Another design would be to etch the microchannels on the glass or plastic substrate while keeping a solid barrier in PDMS. Fabrication of microfluidic device is simpler and easier to use if it can be used with any flat substrate. The fabrication of channels in substrate will require access to cleanroom and sophisticated instruments that most biology laboratories do not have access to. If the physical barrier device can not maintain fluidic integrity, the researcher can load different amounts of liquid to the chambers such that slow flux of liquid counteracts the mixing of agonists into the soma chamber. For example, we can add slightly more volume of liquid into the soma chamber compared to the neurite chamber (into which insults will be introduced) to generate hydrostatic pressure such that the insults from the neurite chamber do not make it across the barrier.

Design of the chamber As discussed in the previous section, two distinct chamber designs are depicted, but other designs or a hybrid of both designs is also feasible. The two designs depicted have distinct advantages and disadvantages. Although the design and fabrication of the virtual barrier chamber is simpler, the experiment using this device is more labor and equipment intensive. Most important, this chamber requires a dedicated syringe pump (or other suitable ways to deliver two or more streams containing media and insult in controlled manner) such that only one experiment can be performed with one device. Since the virtual barrier exists only for constant perfusion of fluids, the amount of reagent required for this method can be significant (~several ml), comparable to that for conventional methods.

In comparison, the physical barrier design allows experiments in a parallel fashion, that is several chambers can be prepared, loaded with neurons, and yet each chamber can be used to test different experimental conditions. The main drawback of the physical barrier design is that fabrication of the "master" mold is slightly more challenging and it takes considerable engineering efforts to optimize the chamber design to guarantee that the chambers are fluidically isolated. To determine an optimal design the physical barrier chamber can be extensively tested using fluorescent and isotope labeled dyes.

Viability of Neurons Inside the Microfabricated Device.

Figure 2:
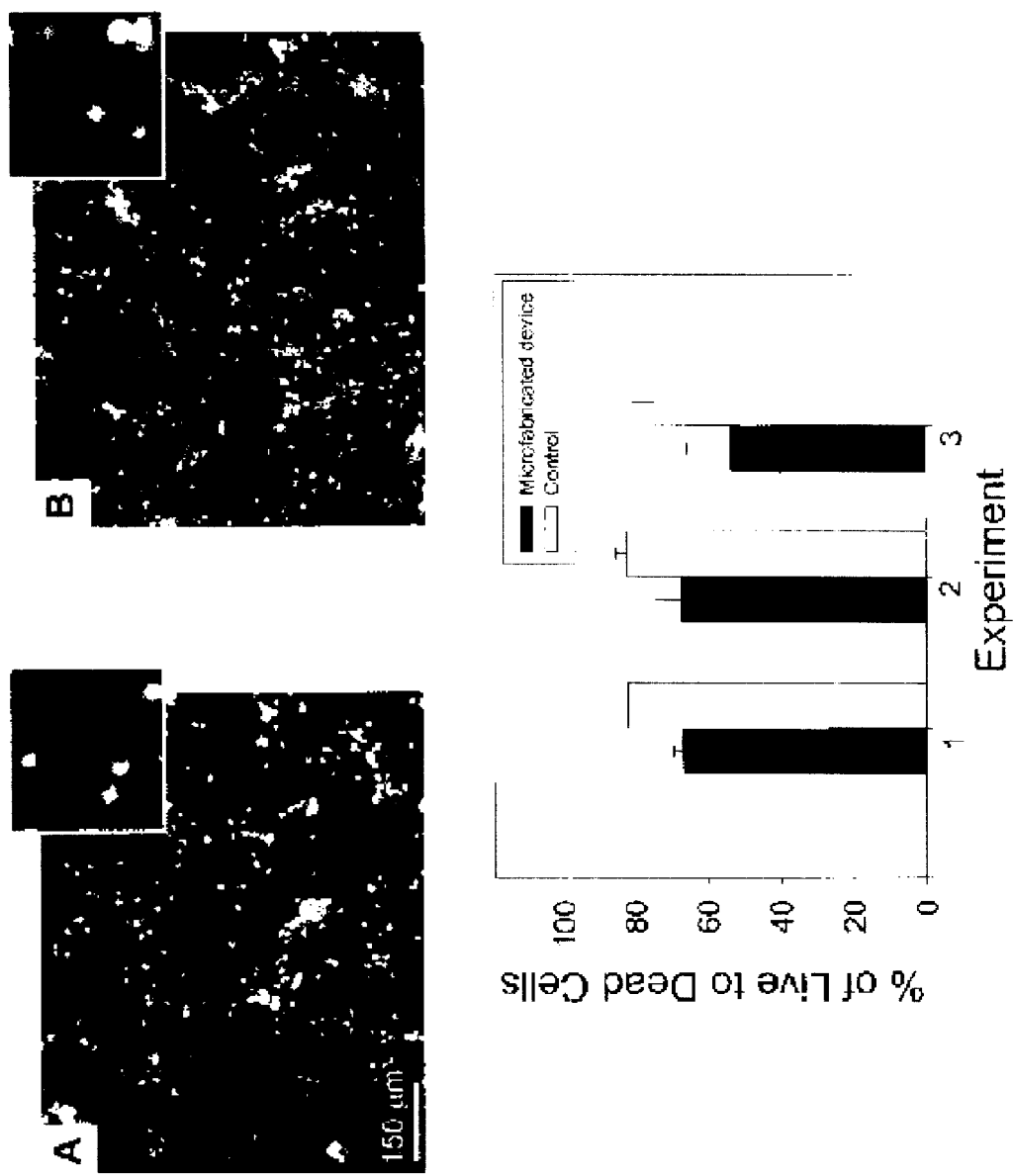
FIG. 2 depicts viability of neurons inside the microfabricated device configured in accordance with one embodiment of the invention.

Viability of neurons in the device is important because it demonstrates that the neurons are healthy and not adversely affected by the device microenvironment and the materials that were used in fabrication. When the viability of neurons inside the microfabricated device is compared with a control (tissue culture dish) after 7 days of culture an estimate as to viability can be determined. The viability was assessed using calcein AM and ethidium homodimer live/dead stain (Molecular Probes). Results are shown in FIG. 2. Viability in the device was approximately 10-20% lower than in tissue culture controls. The viability of neurons can be very sensitive to cell density. To get accurate viability data, tests where conducted using similar cell densities in the devices and controls. A plating density of $3\_10^6$ cells/mL was used for the devices and diluted this 1:25 for the tissue culture controls which gave us an average of $1.5\_10^5$ cells/cm2 for both devices and controls. For each experiment, three devices and one control were used. If the three devices were judged to be equivalent, live/dead staining was done on only one of the samples. Morphologically, the cells in the devices were equivalent to the controls as shown in FIGS. 2A,B. The slightly lower viability inside the devices may be due to increased salt concentration from evaporation and lower nutrient and gas exchange due to the smaller total volume of media. Also, an increased ratio of dead cells may get trapped in the device because of the small compartment height (100 um).

Targeted Insult Application, Isolation, and Characterization.

The neuronal device configured in accordance with at least one embodiment of the invention allows users to initiate targeted insults by isolating the insult in the neuronal compartment using hydrostatic pressure or some other way to minimize migration/diffusion into other compartments (e.g., the somal compartment). To prepare the device for initiating such insults, the user typically seals the device top to a culture dish. For instance, the user may contact seal the PDMS top to the polylysine-coated tissue culture dish. The microfabricated device may then be filled with PBS (_200 uL in each somal and neuritic chamber) and placed in a water-saturated incubator for 12 h for the fluid levels to equalize. Once the device is appropriately prepared, the following exemplary procedure can be used to create hydrostatic pressure between the chambers: a quantity of PBS (e.g., appox. 125 uL) may be added to the somal compartment, dividing the volume between the two reservoirs. Then, a quantity (e.g., approx 100 uL of) of fluorescein (6 uM) in PBS can be quickly added to the neuritic compartment, again, dividing the volume between the two reservoirs. The slightly higher volume on the somal side caused a slow net flow of liquid from the somal to the neuritic compartment that acts against leakage or diffusion of fluorescein from the neuritic to the somal compartment.

Figure 3:
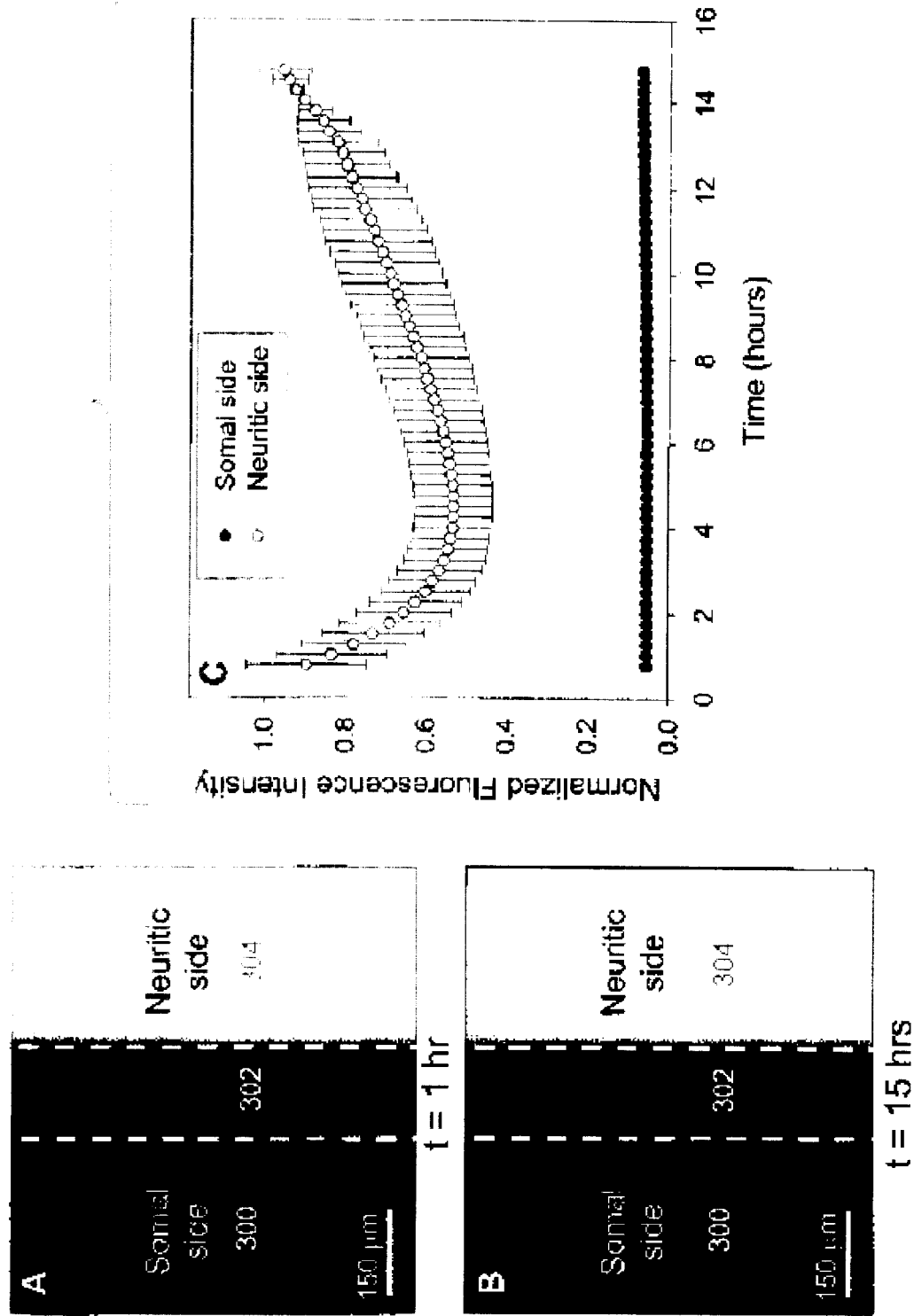
FIG. 3 illustrates fluidic isolation using fluorescence intensity measurements of fluorescein (400 Da) in somal and neuritic compartments.

To determine effectiveness fluorescence images can be taken every half hour for over 15 h using an exposure time of 200 ms with a FITC filter at three separate locations in each side of the somal and neuritic chamber. Intensity measurements can be obtained by recording the average intensity reading of each image. FIG. 3 illustrates fluidic isolation using fluorescence intensity measurements of fluorescein (400 Da) in somal and neuritic compartments. The left side is the somal chamber (300), and the right is the neuritic chamber (304). The dotted white line delineates the boundaries of the barrier (302). (A) The initial fluorescence micrograph (t) 1 h) shows that fluorescein is isolated to the neuritic compartment. (B) A fluorescence micrograph of the same region after 15 h shows that the insult is still isolated to the neuritic compartment. (C) shows the fluorescence intensity of fluorescein in the somal and neuritic compartment as a function of time (306). The fluorescence intensity in the somal side at background levels (e.g., below 7% of the maximum intensity (i.e., noise level)) for over 15 h, indicating that there is no leakage of fluorescein into the somal compartment during this period. The fluorescence intensity of fluorescein in the neuritic compartment decreases to 50% of the maximum due to dilution by the net flow of fluid from the somal compartment. Similar results were obtained for devices on glass (data not shown). The graph indicates that fluorescein is isolated in the neuritic side throughout the period of measurement, but could sustain such isolation for longer periods of time.

Figure 4:
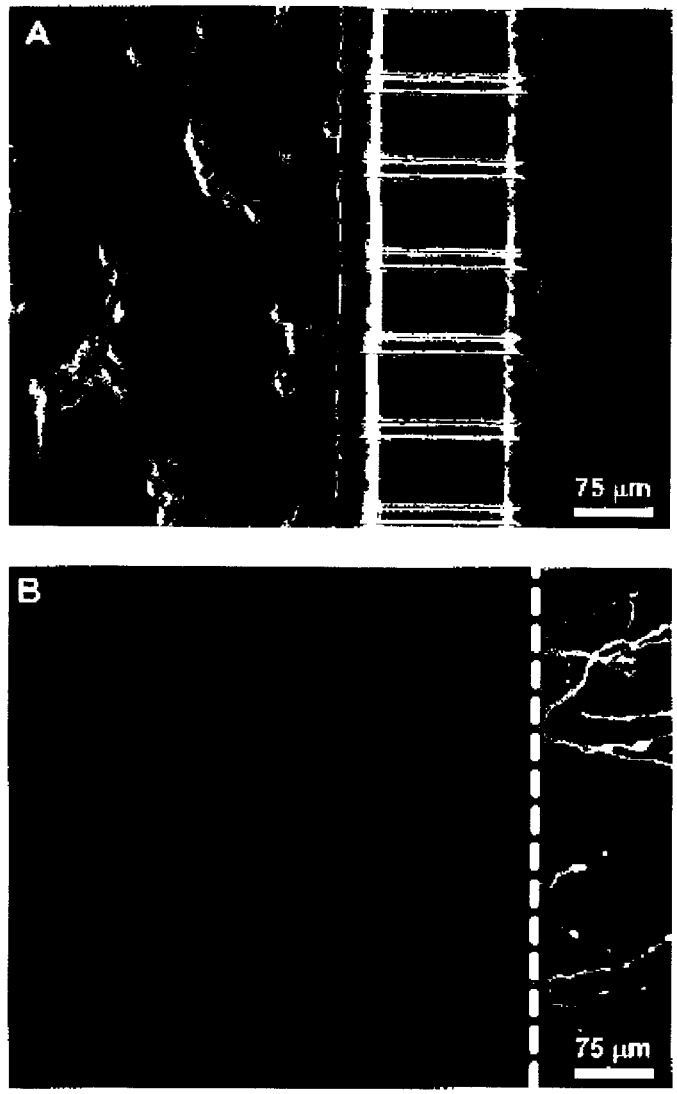
FIG. 4 illustrates a demonstration of neuronal culture inside the microfabricated device and effectiveness of neuritic insult containment.

There are various ways to illustrate the function and effectiveness of the device described herein. In one embodiment of the invention, neurons can be cultured in the microfabricated device in a manner that allows the neurites to extend over to the neuritic compartment. FIG. 4 illustrates a demonstration of neuronal culture inside the microfabricated device and effectiveness of neuritic insult containment.

Calcein AM and Texas Red dextran (MW) 10 kDa) can be added to the neuritic chamber for better visibility before taking the micrographs. A positive hydrostatic pressure difference can be set up between the somal and neuritic chambers as explained in FIG. 3. FIG. 4A is a phase contrast micrograph of the neurons in the microfabricated device after a period if time in culture (e.g., 4 days). Texas Red dextran (10 kDa) and calceinAM (1 kDa) was added into the neuritic compartment 1 h before taking the fluorescence micrograph, FIG. 4B. A slight pressure head, corresponding to a volume differential of 20 uL of medium, was established in the somal side in order to ensure that dextran or calcein AM did not migrate from the neuritic to the somal side. Texas Red dextran was used to simulate the insult in the neuritic compartment and is clearly delineated by the barrier boundary (FIG. 4B). Since calcein AM was added to the neuritic compartment, only the neurons with processes entering this compartment were illuminated. The phase contrast image shows additional neurons that were not stained with calcein AM because they did not have processes extending into the neuritic compartment; this illustrates that the neuritic compartment is fluidically isolated.

Substrate Micropatterning.

In addition to simply isolating somas from their processes, embodiments of the invention are able to pattern the growth of neurites on the substrate inside the microfabricated device. Micropatterning of the cells and their processes facilitates identification of cells and improves visualization of results. For instance, if one needs to investigate the disruption in transport of cellular cargos such as mitochondria after injury to distal neuronal processes, it is helpful to determine the direction of transport by identifying the relative position of a soma with respect to its neurites. In a random culture on a tissue culture dish, due to entangled network neuritis and axons, this simple determination cannot be performed easily. If the cell body is positioned in one side of the device (on the somal side) and its processes are guided and oriented in a predetermined direction, the determination of anterograde or retrograde transport can be greatly simplified.

Figure 6:
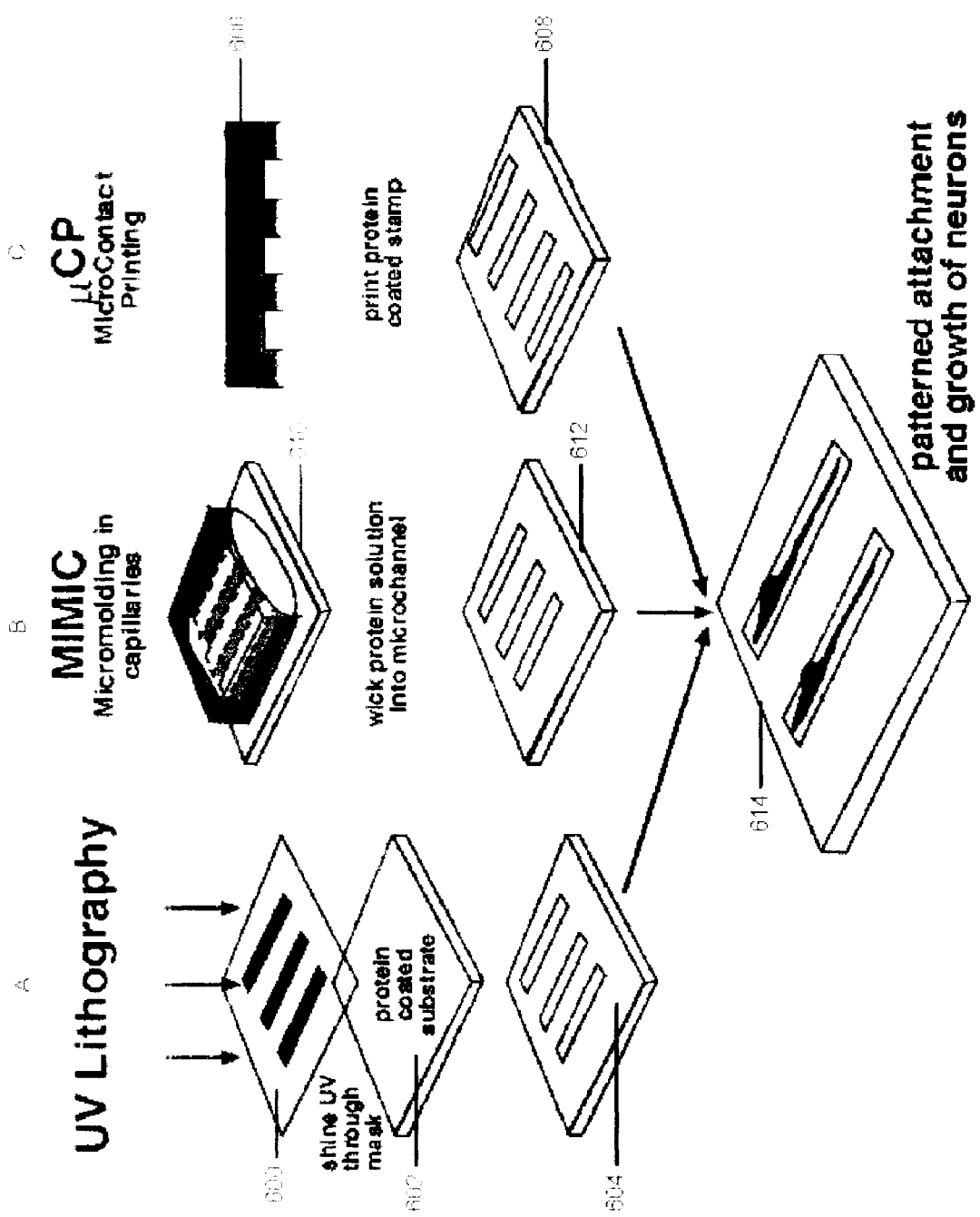
FIG. 6 illustrates a schematic of the different approaches for patterning neurons to control direction of growth.

FIG. 6 illustrates a schematic of the different approaches for patterning neurons. Photolithography (A) micromolding in capillaries (MIMIC) (B), microcontact printing (B), and any other methodology that accomplishes the same or a similar result can be used to pattern proteins that promote selective neuron attachment and growth and confine neurite outgrowth.

When photolithography is used to generate such patterns a poly-lysine or laminin-coated glass or polystyrene substrate is overlayed with a mask (600) (e.g., chrome on quartz photomask) and illuminated with UV light (e.g., a low pressure mercury lamp). A photomask (600) that has strips of opaque regions results in a positive pattern of protected protein strips. Laminin (602) under the transparent area of the photomask will be exposed to UV and become inactivated (604), losing both its neurite outgrowth-promoting activity and much of its reactivity with anti laminin antibodies. UV exposed poly-lysine also shows similar properties.

Micromolding in capillaries (MIMIC) represents an alternative to photolithography that can pattern proteins as well as other biological molecules. In MIMIC, an elastomeric mold (PDMS) is placed on the substrate with a relief structure in the mold that forms a network of empty channels. With the correct channel geometry an aqueous solution placed on one side of the channels will fill them by capillary action. The solution is then left in the channels for a set amount of time to allow absorption onto the surface.

Another exemplary method of patterning, microcontact printing, can be used to create poly-L-lysine lines on coverglass. Microcontact printing uses an elastomeric stamp (PDMS with a patterned relief structure on its surface) to print a variant of molecules with micron resolution. An elastomeric stamp can be made by curing PDMS against a microfabricated master. The surface is coated with the desired molecules (for printing proteins, the PDMS stamp is exposed to oxygen to plasma to render its surface hydrophilic) and placed in conformal contact with the substrate. If a stamp with strips of lines (raised regions) separated by spaces (recessed regions) is used as shown in the figure, the molecules/proteins from the raised region will be transferred onto the host substrate. Microcontact printing has the advantage of simplicity and convenience: once the stamp is available, multiple copies of the protein pattern can be produced using a straightforward method. Microcontact printing works particularly well on glass substrates due to the smooth surface of the glass.

Figure 5:
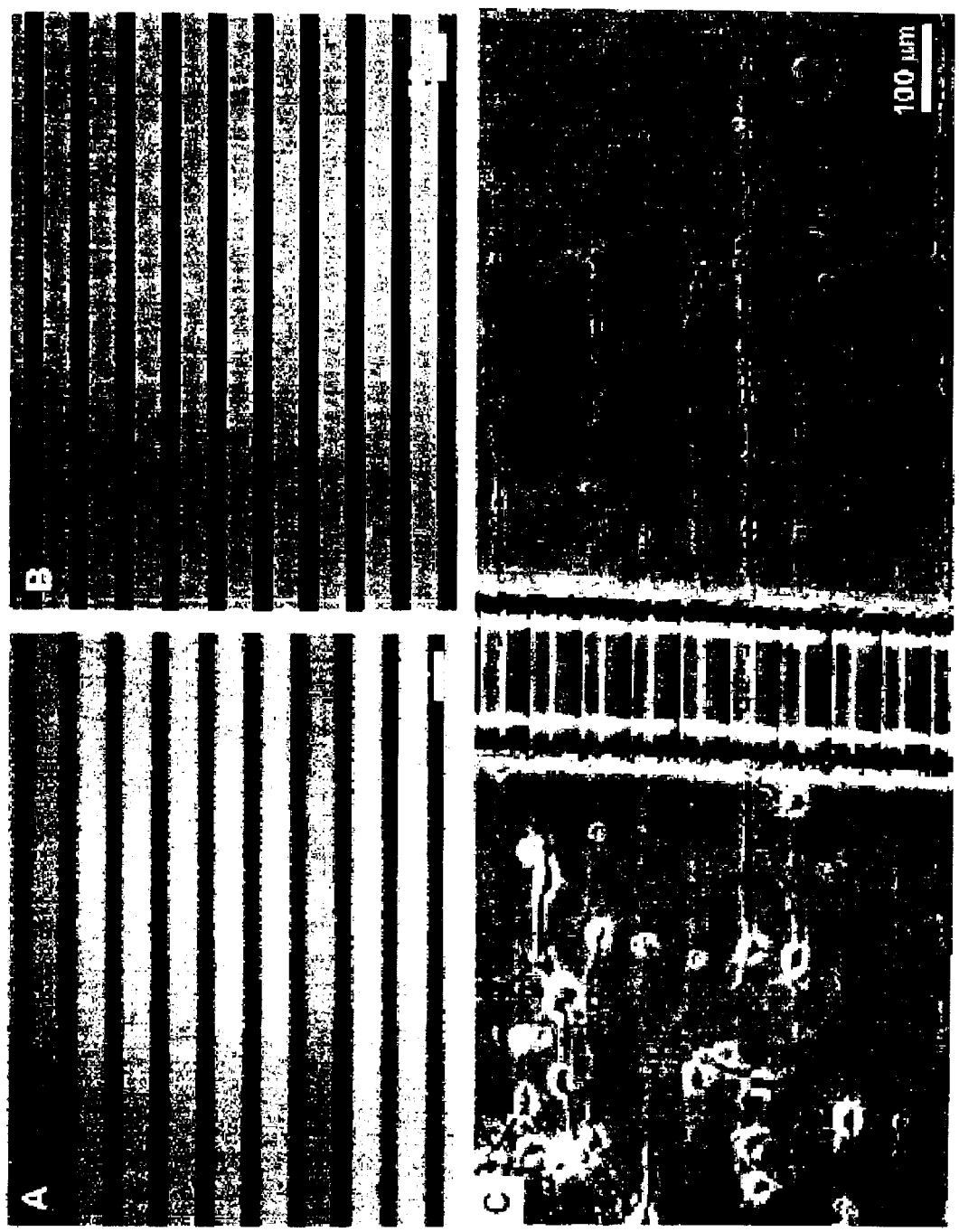
FIG. 5 illustrates that when using substrate micropatterning the microfabricated device allows oriented growth of neuron processes across fluidically isolated chambers.

FIG. 5 illustrates that when using substrate micropatterning the microfabricated device allows oriented growth of neuron processes across fluidically isolated chambers. The invention contemplates various mechanisms for substrate patterning, however in one exemplary embodiment (see e.g., FIG. 5A) fluorescence micrograph of poly-lysine patterned lines conjugated with FITC on a polystyrene tissue culture dish. MIMIC can be used to pattern the lines with widths of 25 um and a spacing of 25 um. Bright lines indicate the region of patterned polylysine conjugated with FITC. FIG. 5B illustrates fluorescence micrograph of microcontact-printed polylysine lines conjugated with FITC on a glass coverslip. Microcontact printing can be used to pattern the lines with widths of 25 um and a spacing of 25 um. FIG. 5C shows a phase micrograph of neurites crossing the barrier from the somal to the neuritic chamber via the grooves while following the polylysine pattern on a tissue culture dish patterned by MIMIC (e.g., 25 um wide lines with 25 um spacing).

As was briefly mentioned above and will now be described in more detail, embodiments of the invention use MIMIC to pattern tissue culture dishes with polylysine. MIMIC represents a technique that can pattern protein and other biological molecules.4,5,10. In MIMIC, the PDMS mold is placed on the surface of the plastic substrate and makes conformal contact with the substrate. The relief structure in the mold forms a network of empty channels. It is advisable to use sterile conditions for creating our MIMIC patterns. When the PDMS mold is removed, a pattern of protein remains on the substrate. FIG. 5A shows a fluorescence micrograph of FITC, which was conjugated to amine groups in polylysine. Microcontact printing (uCP) is an efficient method for patterning proteins, polymers, and self-assembled monolayers (SAMs) .4,5,10 microcontact printing uses an elastomeric stamp (PDMS with a patterned relief structure on its surface) to print a variety of molecules with micron resolution. An elastomeric stamp can be made by curing PDMS against a microfabricated master. The surface is coated with the desired molecules (for printing proteins, the PDMS stamp will be exposed to an oxygen plasma to render its surface hydrophilic) and placed in conformal contact with the substrate. If a stamp with strips of raised regions separated by recessed regions is used, the molecules/proteins from the raised region is transferred onto the host substrate.4,5 FIG. 5B shows the FITC conjugated pattern of polylysine on glass using microcontact printing. FIG. 5C shows the growth of neurites across the barrier, via the grooves, along patterned polylysine lines. The polylysine pattern can be formed in one embodiment of the invention on a tissue culture dish using MIMIC. Patterning of the substrates with polylysine prior to assembly with a PDMS device is simplified because the polylysine pattern can be dried and even sterilized with ethanol. This figure illustrates that the substrate patterning methods (e.g., microcontact printing and MIMIC) can be combined with a microfabricated device to direct the sites of neuronal attachment and the orientation of neurite outgrowth. Combined with fluidically isolated compartments, this approach offers significant advantages over standard open culture methods and other conventional methods for manipulating distinct neuronal microenvironments.

Figure 7:
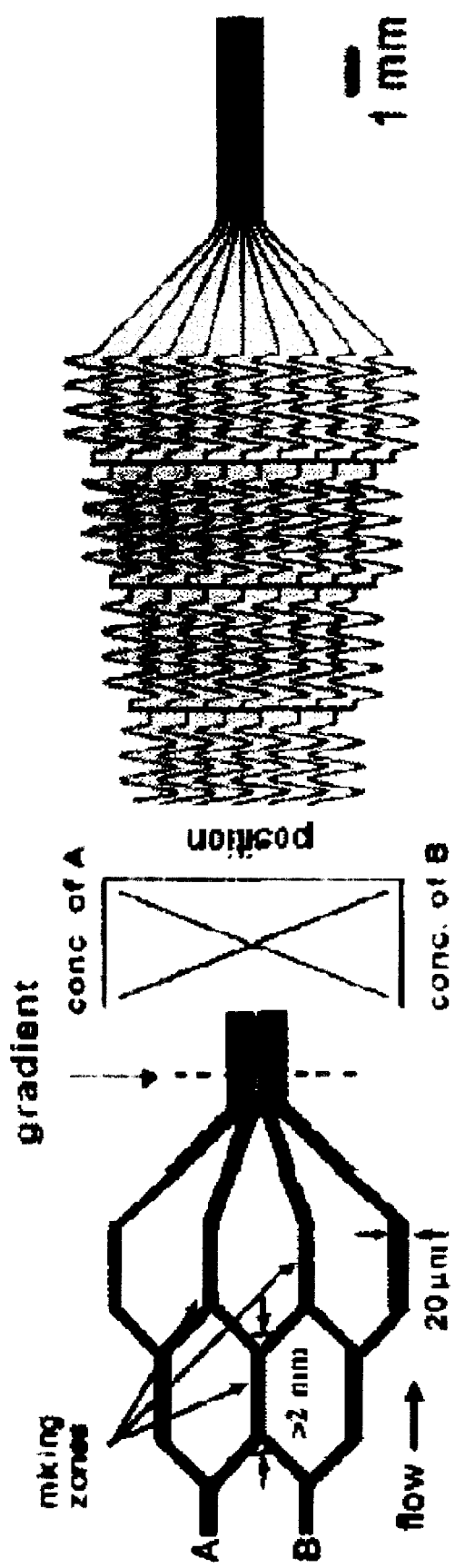
FIG. 7 illustrates a schematic diagram of a microfluidic network and a representative microfluidic generator configured in accordance with at least one embodiment of the invention.

Microfluidic Gradient Generator FIG. 7 illustrates a schematic diagram of a microfluidic network and a representative microfluidic generator configured in accordance with at least one embodiment of the invention. The two incoming channels (A and B) are connected to fluid sources (e.g., dye solutions). As the streams of dye travel down the network they are repeatedly split at the nodes, combined with neighboring streams, and allowed to mix by diffusion in the serpentine channels. When the streams are combined into a single, wide channel after several generations of branching channels, a gradient in concentration of the dye is formed across the channel perpendicular to the direction of flow.

The generation of gradients using a network of microfluidic channels is based on the controlled mixing of laminar flow fluids by repeated splitting, mixing, and recombination of fluid streams. Since exchange of molecules between laminar streams occurs exclusively by diffusion, it is important that the channels are narrow (20-50 um) and the interval of time that two laminar flow streams spend flowing side by side in the serpentine channel is sufficiently long that the fluids mix completely (the length of the serpentine mixing zone was ~10 mm, and flow speeds were between 0.1-1 mm/s).

A small molecule (e.g. fluorescein) diffuses approximately 55 um within one second (using $D=5.0 \times 10^{-6}$ cm2/s for fluorescein). At the end of the broad channel, the fluid is collected in a waste reservoir. The concentration profile at a particular section across the small channels of the network or the broad channel is constant over time (that is the concentrations within the channel are at steady state), because the solutions are continuously added and removed from the system.

Figure 8:
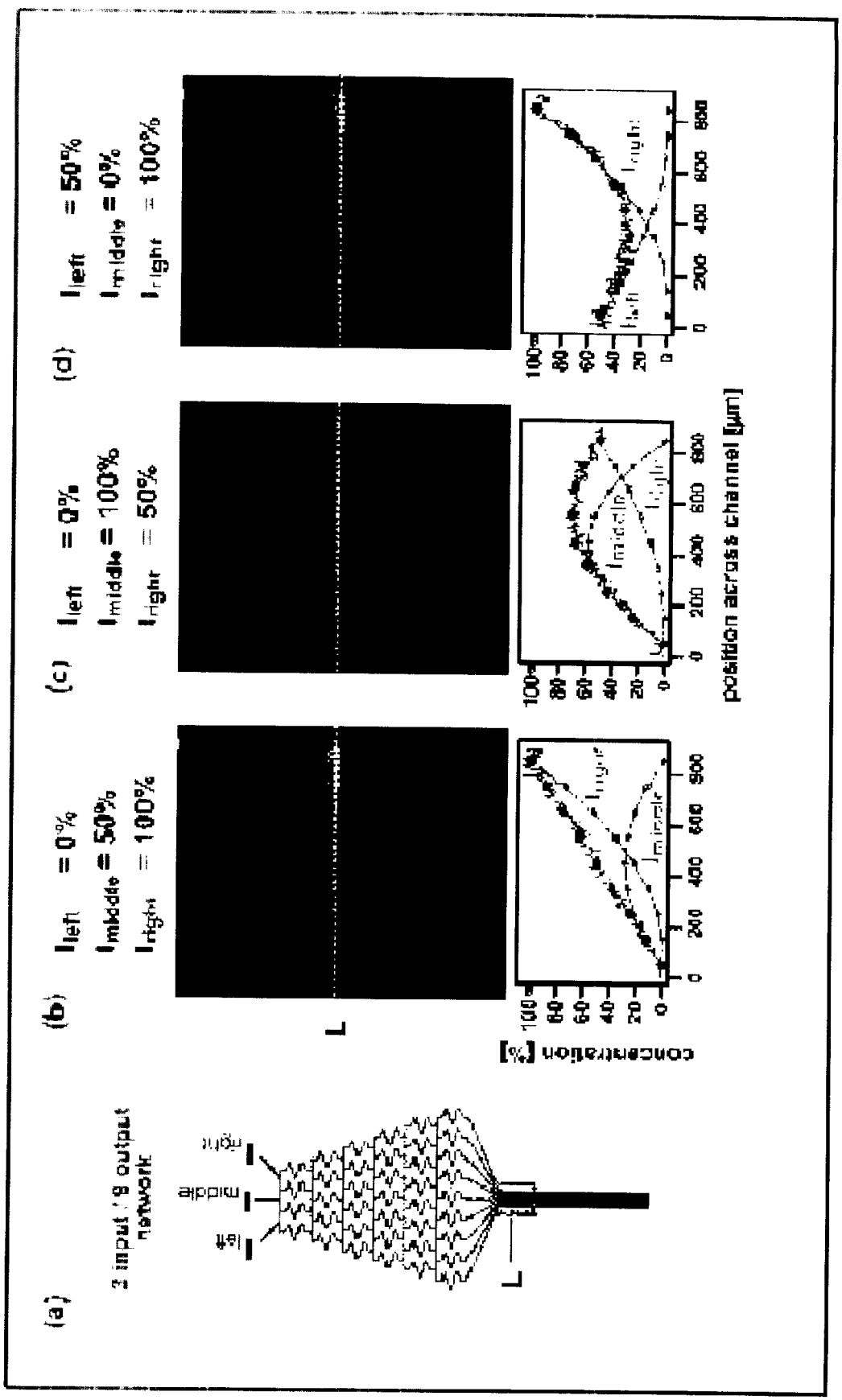
FIG. 8 illustrates fluorescence micrographs showing (b) linear and (c, d) parabolic gradients of fluorescein in solution.

FIG. 8 illustrates fluorescence micrographs showing (b) linear and (c, d) parabolic gradients of fluorescein in solution. The microfluidic network used for generating these gradients had 3 inlets and 9 outlets (a). The concentration of the solutions introduced into each inlet of the microfluidic network is indicated above the micrographs. The plots below the micrographs show the corresponding fluorescence intensity profile (green line) across the broad channel (900 um wide) 500??m downstream (L, white dotted line) from the junction. The theoretically calculated concentration profiles of fluorescein are shown as black, round dots. The gray lines and dots in the graphs show the calculated contribution of the individual inputs to the overall profile. The flow rate in the broad channel is 1 mm/s. using a network of microfluidic channels is based on the controlled mixing of laminar flow fluids by the repeated splitting, mixing, and recombining of fluid streams. FIG. 8 shows three distinct concentration profiles generated using a network having three inlets and nine outlets; the gradients were obtained by permuting the order at the inlets of three different solutions containing 100, 50, and 0% fluorescein (fluorescein in 100 mM NaHCO3 buffer, pH 8.3). The purpose of this type of microfluidic device is to split, combine, and mix the solutions introduced at the inlet in a controlled way. While keeping the number of inlets low, the splitting in the pyramidal network increases the number of streams carrying different concentrations and being brought together in the broad channel. As a result, complex gradients can be approximated with step-gradients made of a large number of small steps. The range of gradient shapes that can be produced using this method include linear, parabolic, periodic, and others.

Figure 9:
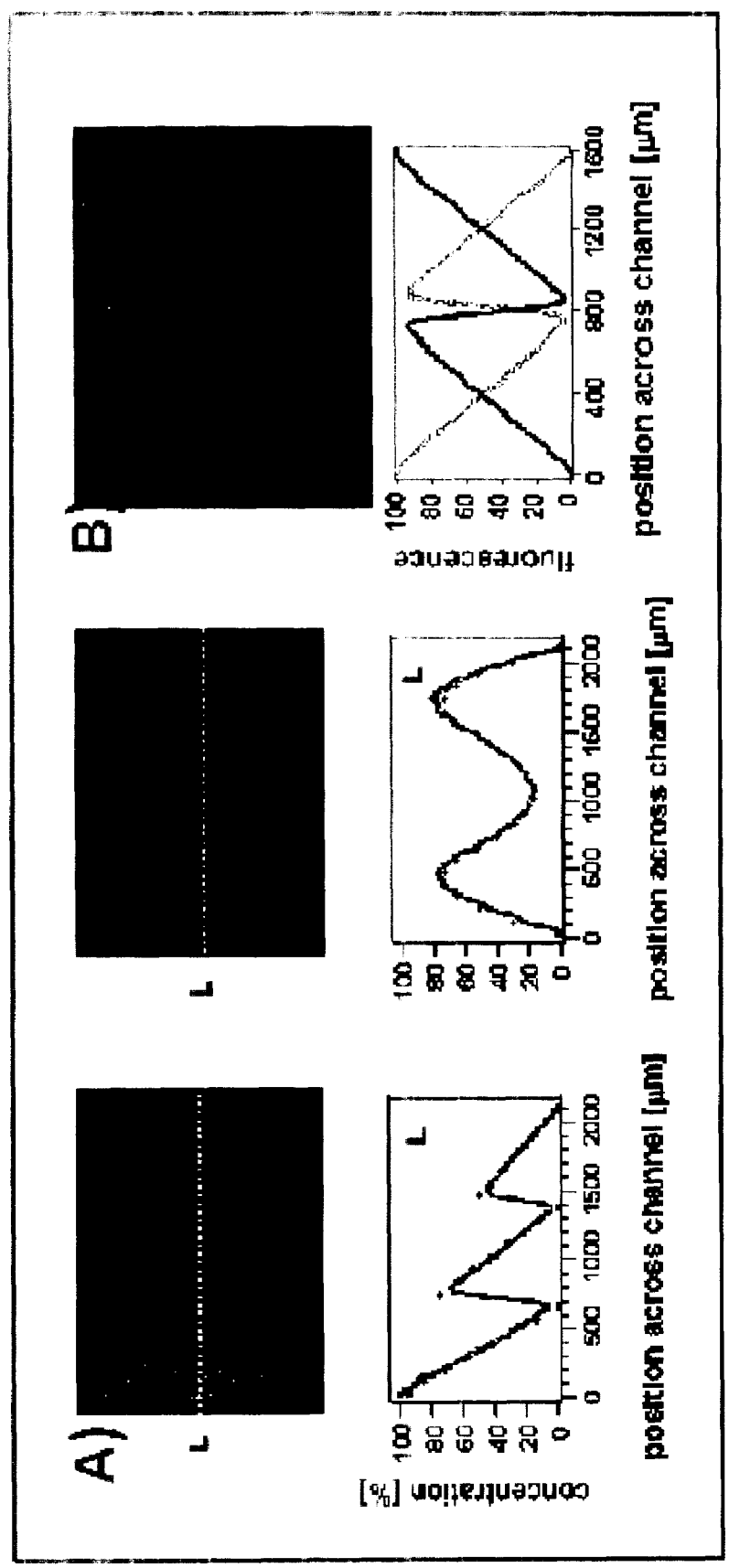
FIG. 9 illustrates fluorescence micrographs of complex gradients possible with the microfluidic approach.

FIG. 9 illustrates fluorescence micrographs of complex gradients possible with the microfluidic approach. (A) Micrographs of two different periodic gradients consisting of linear parts (saw-tooth) and parabolic parts (camel-back). (B) Micrograph of periodic, overlapping saw-tooth gradients of fluorescein (green) and rhodamine (red). The plots below the micrographs show the corresponding fluorescence intensity profile across the channels. The calculated (round dots) and experimental gradients showed good agreement in all experiments. FIG. 9 shows three examples of complex concentration gradients using this approach. Saw-tooth and saddle shape gradients can be readily produced. The main advantage of generating chemical gradients using the microfluidic system is that precise gradients can be set up (micron-scale, relevant for cell biology) and maintained for several hours. In addition complex shapes and overlapping gradients can be created.

Figure 10:
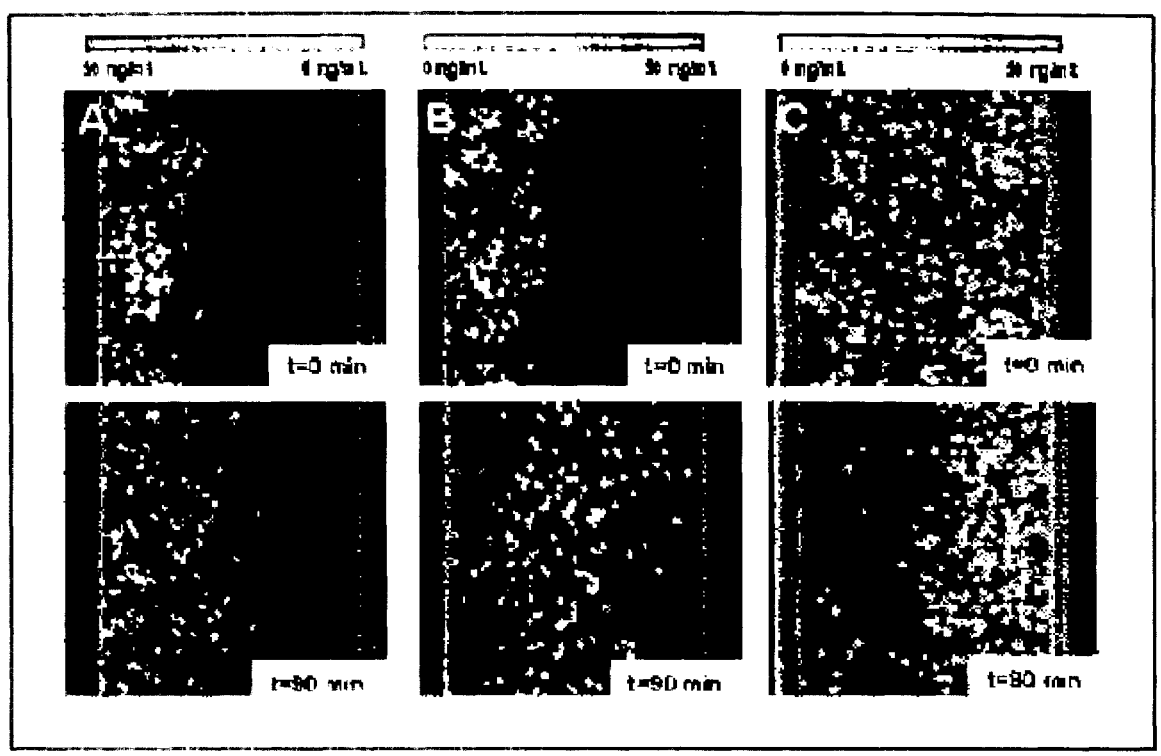
FIG. 10 illustrates the effect of linearly decreasing concentration of IL-8 on neutrophil migration.

To demonstrate the feasibility of using the gradient generator microfluidic chamber for studying live cells, this microfluidic device was used to successfully observe chemotaxis of neutrophils in a gradient of chemokine. The successful demonstration of neutrophil migration in an IL-8 gradient using the microfluidic chemotaxis chamber illustrates its enormous potential in investigating the behavior of neurons in a controlled microfluidic environment and the guidance of neurite outgrowth in a gradient of neurotrophins or axon guidance molecules. The microfluidic device can be placed on a microscope during the experiment and time-lapse micrographs taken at 15 sec intervals. Computer controlled syringe pump is used to infuse the media and chemokine into the device. The cells were placed in a narrow band (FIGS. 10A and B) along the left edge of the channel at the beginning of the experiment and allowed to migrate across the channel for 90 minutes. The effect of linearly decreasing concentration of IL-8 on neutrophil migration is shown in FIG. 10A. The cells were initially placed on the side with the higher concentration of IL-8 and allowed to migrate. After 90 minutes, the cells remained on the left side of the channel. In sharp contrast, FIG. 10B shows the effect of reversing the linear gradient established in the previous experiment. The cells were initially placed on the left side with the lower concentration of IL-8. Ninety minutes after the introduction of the gradient, most of the cells were moving across the device towards the side with the higher concentration. In FIG. 10C the neutrophils were initially randomly distributed throughout the channel and a linear gradient of IL-8 was applied. After 90 minutes most neutrophils have moved towards the side with the higher concentration of IL-8. Furthermore, the quantitative migration data obtained from these preliminary experiments with neutrophils (i.e. migration speed) agree well with the published values reported in the literature. Human cancer cells chemotax in a similar manner when exposed to gradients of a variety of growth factors (data not shown). The successful demonstration of neutrophil migration in an IL-8 gradient using the microfluidic chemotaxis chamber illustrates its enormous potential in investigating the behavior of neurons in a controlled fluidic microenvironment.

Conclusion Embodiments of the invention are directed to a microfabricated neuronal culture device that allows directed growth of neurites and isolation of neurites from their cell bodies. The device can use hydrostatic pressure to isolate insults to one compartment and, thus, expose localized areas of neurons to insults. Due to the high resistance of the microgrooves for fluid transport, insults are contained in the neuritic compartment without appreciable leakage into the somal compartment for a certain period of time (e.g., over 15 h). One embodiment of the invention uses poly-lysine patterning in combination with the microfabricated device to facilitate identification and visualization of neurons. The ability to direct the sites of neuronal attachment and the orientation of neurite outgrowth by micropatterning techniques, combined with fluidically isolated compartments within the culture area, offers significant advantages over standard open culture methods and other conventional methods for manipulating distinct neuronal microenvironments.

What is claimed is:

1. A multi-compartment microfluidic device for enabling fluidic isolation among interconnected compartments within the device comprising:
   a substrate coupled with an optically transparent device;
      said substrate comprising a micropatterned cell-adherent coating configured to direct cell attachment;
      said optically transparent device comprising a first microfluidic region having a first plurality of entry reservoirs for accepting or extracting a first volume of fluid;
      said optically transparent device further comprising a second microfluidic region, said second microfluidic region having a second plurality of entry reservoirs for accepting or extracting a second volume of fluid that is less than said first volume of fluid to create hydrostatic pressure;
      a barrier region that couples said first microfluidic region with said second microfluidic region in a way that enables a biological specimen to simultaneously extend across said first microfluidic region, said barrier region and said second microfluidic region; and,
      said barrier region comprising a plurality of microgrooves having a width and height that enables said second volume of fluid to be fluidically isolated from said first volume of fluid via said hydrostatic pressure maintained via said at least one embedded microgroove wherein said first microfluidic region, said second microfluidic region, said first plurality of entry reservoirs, said second plurality of entry reservoirs and said barrier region are fabricated into said optically transparent device.

2. The multi-compartment microfluidic device of claim 1 wherein said first microfluidic region and said second microfluidic region are dispose parallel to one another and coupled with said barrier region.

3. The multi-compartment microfluidic device of claim 1 wherein said at barrier region comprises a length of not less than 50 µm.

4. The multi-compartment device of claim 1 wherein at least one of said plurality of microgrooves comprises dimensions less than 10 µm in height.

5. The multi-compartment microfluidic device of claim 1 wherein said biological specimen comprises a cellular structure.

6. The multi-compartment microfluidic device of claim 5 wherein said first volume of fluid is applied to a cell body domain of said cellular structure and said second volume of fluid is applied to a cellular extension or outgrowth domain of said cellular structure.

7. The multi-compartment microfluidic device of claim 6 wherein said cellular extension or outgrowth domain comprises pseudopod or lamellipodium.

8. The multi-compartment microfluidic device of claim 5 wherein said cellular structure comprises a nerve cell.

9. The multi-compartment microfluidic device of claim 8 wherein said first volume of fluid is applied to a somal domain of said nerve cell and said second volume of fluid is applied to an neuritic region of said nerve cell.

10. The multi-compartment microfluidic device of claim 9 wherein said somal domain comprises a nerve cell body.

11. The multi-compartment microfluidic device of claim 9 wherein said neuritic region comprises an axonal domain.

12. The multi-compartment microfluidic device of claim 8 wherein synapses of said nerve cell are isolated in said second microfluidic region.

13. The multi-compartment microfluidic device of claim 1 wherein said cell-adherent coating comprises any one or more selected from the group consisting of polylysine, laminin, collagen, fibronectin, integrin, polyamine, and polyornithine.

14. A method for enabling fluidic isolation among interconnected compartments within a multi-compartment microfluidic device comprising:
   forming a micropatterned cell-adherent coating configured to direct cell attachment onto a substrate;
   coupling said substrate with an optically transparent device;
   forming into said optically transparent device a first microfluidic region having a first plurality of entry reservoirs for accepting or extracting a first volume of fluid;
   forming into said optically transparent device a second microfluidic region, said second microfluidic region having a second plurality of entry reservoirs for accepting or extracting a second volume of fluid that is less than said first volume of fluid to create hydrostatic pressure;
   forming into said optically transparent device a barrier region that couples said first microfluidic region with said second microfluidic region in a way that enables a biological specimen to simultaneously extend across said first microfluidic region, said barrier region and said second microfluidic region; and, isolating fluidically said first volume of fluid from said second volume of fluid using said barrier region comprising a plurality of microgrooves having a width and height that enables said second volume of fluid to be fluidically isolated from said first volume of fluid via said hydrostatic pressure maintained via said at least one embedded microgroove wherein said first microfluidic region, said second microfluidic region, said first plurality of entry reservoirs, said second plurality of entry reservoirs and said barrier region are fabricated into said optically transparent device.

* * * * *